(12) United States Patent
Larsen et al.

(10) Patent No.: US 7,589,053 B2
(45) Date of Patent: Sep. 15, 2009

(54) PRE-SOAPED, DISPOSABLE LUFFAH

(75) Inventors: Bruce T. Larsen, Las Vegas, NV (US); Bryan Larsen, Vegas, NV (US)

(73) Assignee: Larsen Concepts, LLC, Las Vegas, NV (US)

( * ) Notice: Subject to any disclaimer, the term of this patent is extended or adjusted under 35 U.S.C. 154(b) by 0 days.

(21) Appl. No.: 11/836,701

(22) Filed: Aug. 9, 2007

(65) Prior Publication Data

US 2009/0042760 A1 Feb. 12, 2009

(51) Int. Cl.
*A47K 7/02* (2006.01)
(52) U.S. Cl. .......................... 510/441; 15/118; 15/209; 15/244.2; 15/277
(58) Field of Classification Search ................ 510/441; 424/443; 15/209, 144, 227
See application file for complete search history.

(56) References Cited

U.S. PATENT DOCUMENTS

| | | | | |
|---|---|---|---|---|
| 2,593,689 | A | * | 4/1952 | Mitchell .................... 206/422 |
| 3,233,727 | A | * | 2/1966 | Wilson ....................... 215/247 |
| D257,227 | S | * | 10/1980 | Youngberg .................. D9/668 |
| 4,377,598 | A | * | 3/1983 | Nugent ....................... 426/108 |
| 5,650,384 | A | | 7/1997 | Gordon et al. |
| 5,716,005 | A | | 2/1998 | McMahan |
| 5,875,511 | A | | 3/1999 | Nejdl |
| 5,944,032 | A | | 8/1999 | Masterson |
| 5,952,090 | A | | 9/1999 | Fan |
| D425,423 | S | * | 5/2000 | Mengeu et al. .............. D9/503 |
| 6,092,717 | A | * | 7/2000 | Lowry ................... 229/120.03 |
| 6,846,784 | B2 | | 1/2005 | Engel et al. |
| 6,883,994 | B1 | | 4/2005 | Grogg |
| 6,902,338 | B2 | | 6/2005 | Puvvada et al. |
| 2003/0000039 | A1 | * | 1/2003 | Borcherds ................... 15/209.1 |
| 2004/0242097 | A1 | | 12/2004 | Hasenoehrl et al. |
| 2005/0000046 | A1 | | 1/2005 | Popovsky et al. |
| 2005/0130536 | A1 | | 6/2005 | Siebers et al. |
| 2005/0238701 | A1 | * | 10/2005 | Kleinwaechter ............ 424/443 |
| 2005/0276827 | A1 | | 12/2005 | Macedo et al. |
| 2007/0039116 | A1 | * | 2/2007 | Woodard et al. .............. 15/227 |

* cited by examiner

*Primary Examiner*—Mark Eashoo
*Assistant Examiner*—M. Reza Asdjodi
(74) *Attorney, Agent, or Firm*—Greenberg Traurig

(57) ABSTRACT

Described is a pre-soaped, disposable luffah. The luffah of the type having a series of ruffles, is impregnated or coated with a cleansing and/or moisturizing agent such that a separate cleansing and/or moisturizing agent does not need to be applied to the luffah. The luffah may be impregnated or coated with the cleansing and/or moisturizing agent in any number of ways including submerging luffahs in a substantially wet, cleansing and/or moisturizing agent or spraying the substantially wet, cleansing and/or moisturizing agent on the luffahs. Once the substantially wet, cleansing and/or moisturizing agent is applied, the luffahs are dried until the substantially wet, cleansing and/or moisturizing agent forms into a substantially dry, cleansing and/or moisturizing agent on the luffah ruffles.

14 Claims, 3 Drawing Sheets

PRE-SOAPED, DISPOSABLE LUFFAH

FIELD OF THE INVENTION

The embodiments of the present invention relate to a ready-to-use, pre-soaped luffah.

BACKGROUND

Luffahs (aka Loofahs, Luffas and bath nets) are now ubiquitous items found in most households. Luffahs are used to apply soap and other cleansers to the body. In general, a luffah is soaked with water and then an ample amount of liquid soap, gel or similar cleansing and/or moisturizing agent is applied to the luffah and then used on the body in a sponge-like manner. However, luffahs are difficult to effectively rinse after use because of the ruffled configuration such that bacteria and other germs can be transferred from one user to another.

Thus, there exists a need for ready-to-use, disposable luffah.

SUMMARY

Accordingly, a first embodiment of the present invention is a cleansing article comprising: a luffah formed of a series of ruffles; said ruffles of said luffah coated with a substantially dry, water-soluable, cleansing and/or moisturizing agent such that said luffah may be used one or more times without an application of additional cleansing and/or moisturizing agent.

Another embodiment of the present invention is a method comprising: applying a substantially wet, cleansing and/or moisturizing agent to at least a portion of a luffah; and drying said luffah such that said applied substantially wet, cleansing and/or moisturizing agent forms into a generally dry, water-soluable, cleansing and/or moisturizing agent on at least a portion of a series of luffah ruffles. In one embodiment, the luffah is then packaged.

The cleansing and/or moisturizing agent may be a soap, body gel, anti-bacterial soap, moisturizing soap and the like. By adding water to the pre-soaped luffah, the luffah is ready to use without the application of a separate liquid cleansing and/or moisturizing agent. As a result, using the luffah in a shower or bath is as simple as unpacking the luffah, placing it in the water stream or tub of water and using it in a sponge-like fashion.

Other variations, embodiments and features of the present invention will become evident from the following detailed description, drawings and claims.

DETAILED DESCRIPTION

It will be appreciated by those of ordinary skill in the art that the invention can be embodied in other specific forms without departing from the spirit or essential character thereof. The presently disclosed embodiments are therefore considered in all respects to be illustrative and not restrictive.

Figure 1:
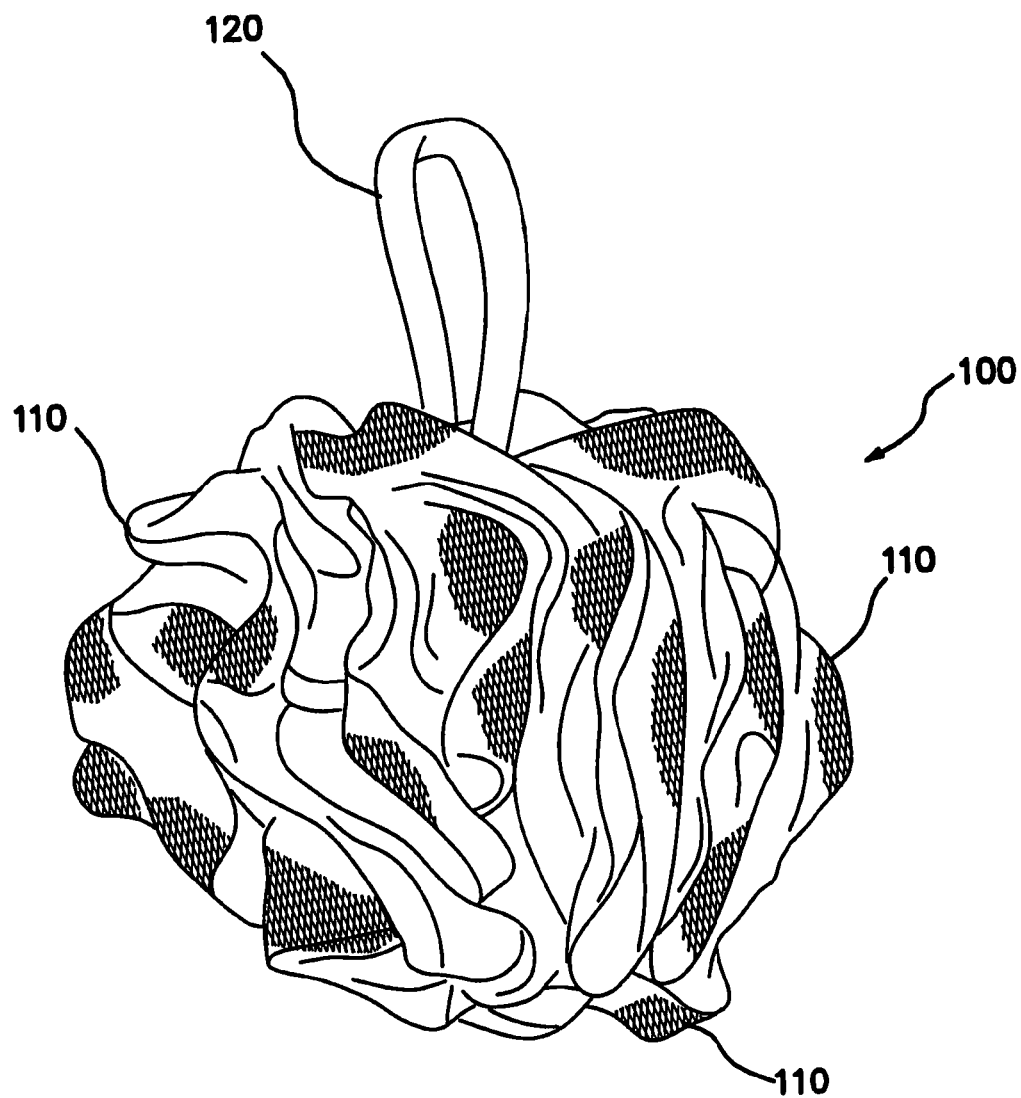
FIG. 1 illustrates a luffah of the type that may be used with the embodiments of the present invention.

Initial reference is made to FIG. 1 illustrating a luffah 100. The luffah 100 is formed of a series of ruffles 110 forming a circular configuration. A string 120 provides means for handling and hanging the luffah 100. The string 120 may also act as a support for maintaining the luffah 100 in its shape and configuration. It will be recognized by those skilled in the art that the luffah 100 may take other shapes and not necessarily include the string.

The embodiments of the present invention comprise a luffah 100 as shown in FIG. 1 with a cleansing and/or moisturizing agent (e.g., clear liquid soap) impregnated therein. In a first embodiment, the luffah 100 is coated or soaked in a substantially wet, cleansing and/or moisturizing agent like clear liquid soap, gel, bath wash, body wash, moisturizer or a similar agent or combinations thereof. Although a clear cleansing and/or moisturizing agent has been found to work well, other non-clear cleansing and/or moisturizing agents are suitable as well. In one embodiment, the luffah 100 is soaked in a pool or container of substantially wet, cleansing and/or moisturizing agent for a time period sufficient to coat the luffah 100. Alternatively, the luffah 100 may be sprayed with the cleansing and/or moisturizing agent. Those skilled in the art will understand that there may be means, other than soaking and spraying, for applying or coating the luffah 100 with the cleansing and/or moisturizing agent. This application is intended to cover those means as well. With the soaking method, after soaking, the luffah 100 is removed from the pool or container of the wet, cleansing and/or moisturizing agent and allowed to dry. Alternatively, the luffah 100 is removed from the spraying process. Depending on the method used, the luffah 100 may be dried with ambient air or a separate heat source may be used to more quickly dry the luffah 100. As a result, the wet, cleansing and/or moisturizing agent dries on the ruffles 110 thereby creating a luffah 100 impregnated or coated with a cleansing and/or moisturizing agent.

In an alternative embodiment, the cleansing and/or moisturizing agent is applied only to a central portion or core of the luffah 100. In this embodiment, the cleansing and/or moisturizing agent dries near the core of the luffah 100 and as such is not on the outer portions of the ruffles 110. With such an embodiment, the luffah 100 has the same feel as a conventional non-soaped luffah. However, once water is applied, the cleansing and/or moisturizing agent quickly disperses throughout the ruffles 110 of the luffah 100.

Figure 2:
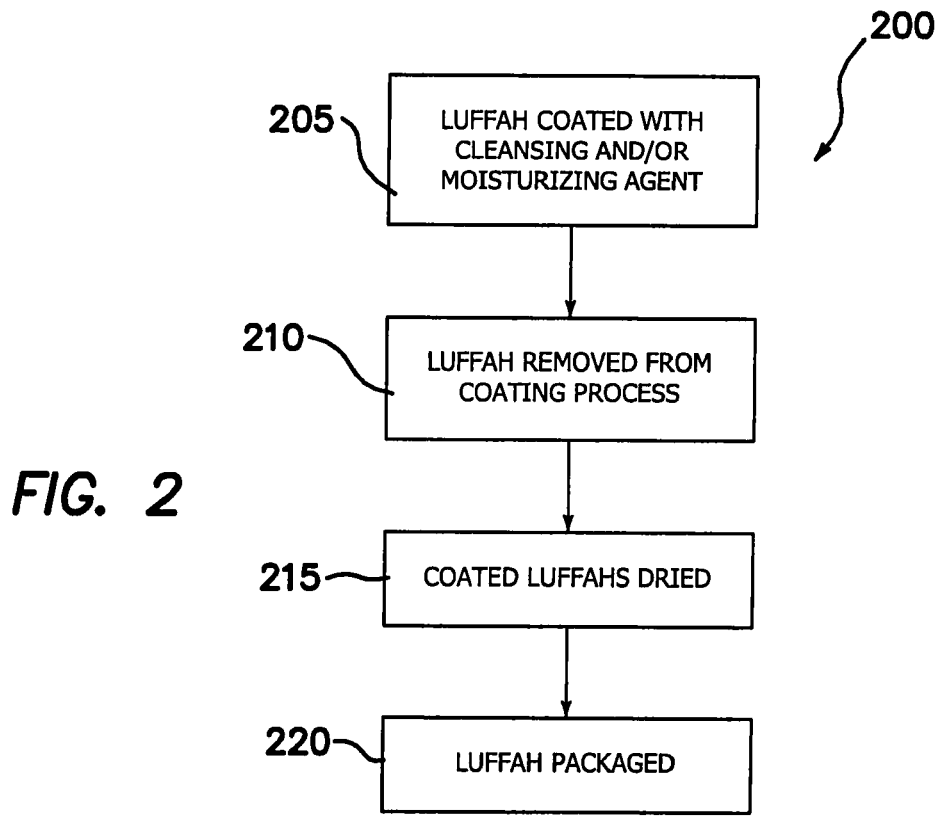
FIG. 2 illustrates a flow chart detailing a method of fabricating a luffah according to the embodiments of the present invention.

FIG. 2 shows a flow chart 200 detailing a method of fabricating a luffah 100 according to the embodiments of the present invention. At 205, a luffah 100 is coated in a cleansing and/or moisturizing agent. In a mass production method, a plurality of luffahs 100 are suspended by their stings 120 from a common support which is then automatically lowered such the plurality of luffahs 100 are partially or completely and simultaneously lowered into a pool or container of cleansing and/or moisturizing agent. The luffahs 100 may also be spray coated with the cleansing and/or moisturizing agent. At 210, the luffah 100 is removed from the cleansing and/or moisturizing agent. With the mass production method, the support is raised such that the plurality of luffahs 100 raises above the pool or container of cleansing and/or moisturizing agent. Alternatively, the spray coating ceases. At 215, the soaked luffahs 100 are dried using ambient air at room temperature or a separate heart source may be used to expedite the drying process. The drying process may also be facilitated by an air blower with or without the aid of heat. At 220, the dried luffahs 100 are packaged. The packaging may be configured to contain one or more luffahs 100.

Figure 3:
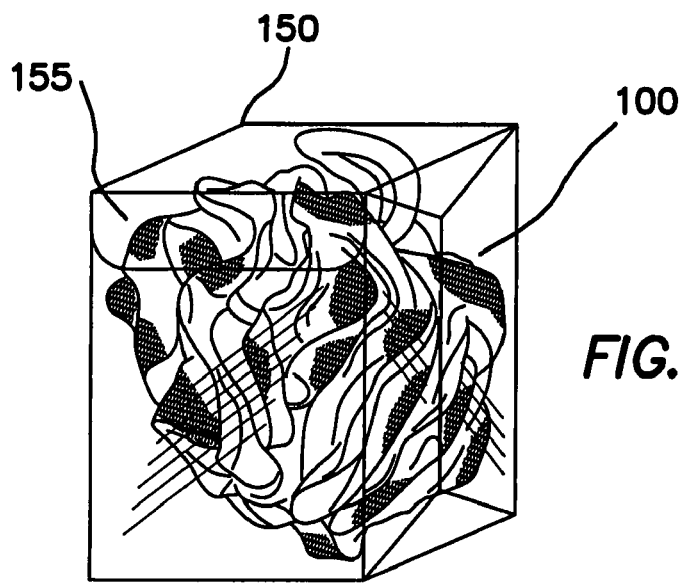
FIG. 3 illustrates an exemplary package for a single luffah.

In one embodiment, as shown in FIG. 3, a single luffah 100 container 150 comprises a transparent material containing the luffah 100. The material used for the container 150 may also be semi-transparent or opaque. The container 150 has an open end 155 temporarily sealed such that the luffah 100 may removed by unsealing the container 150. The container 150 may also depict product instructions, logo, slogans, etc. In one example, the single luffah 100 container 150 is placed in hotel (or motel) rooms for the use of guests. Depending on the hotel, the packaged luffahs 100 may be complimentary or billed to the guest in a manner similar to an honor bar. Hotels may elect to replace used luffahs 100 with new luffahs 100 on a daily basis or at least at the beginning of each new guest visit to the hotel. Hotel logos on the packaging are an ideal method for hotels to exploit their brand.

Figure 4:
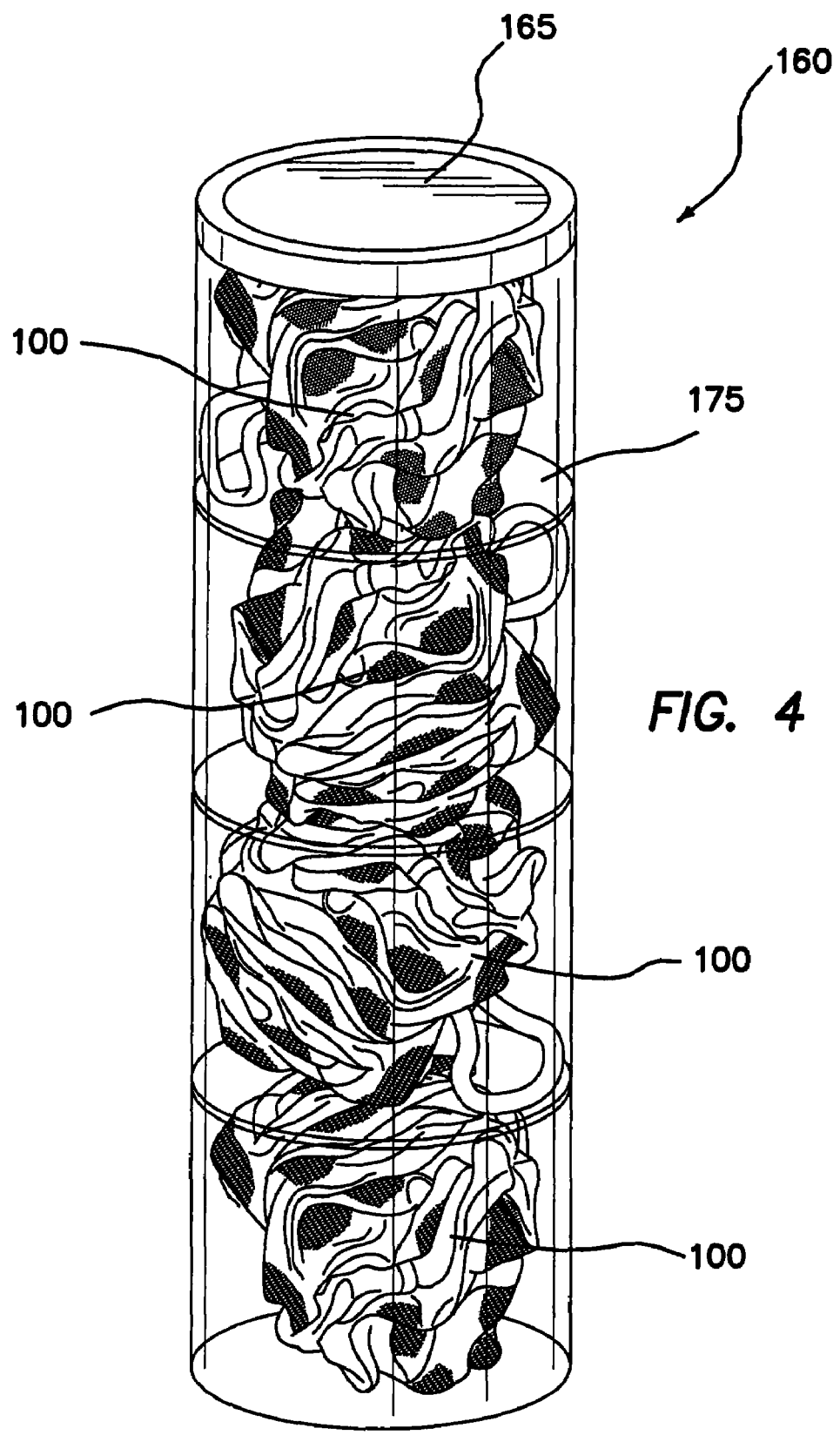
FIG. 4 illustrates an exemplary package for multiple luffahs.

In another embodiment, as shown in FIG. 4, multiple luffah 100 container comprises a transparent (or semi-transparent or opaque) tubular container 160 fabricated of semi-rigid plastic with an open end vacuum-sealed with a pliable plastic or rubber lid 165. A series of spacers 175 may be used to keep the individual luffahs 100 from contacting one another. The vacuum created within the container 160 maintains for extended periods of time, the dry, water-soluable cleansing and/or moisturizing agent impregnated within or coated on the ruffles of the luffahs 100. Again, the tubular container 160 may depict product instructions, logos, slogans and the like. Such a container 160 is suitable for warehousing or inventorying luffahs 100 or presenting them for sale in retail outlets.

Regardless of the manner in which the luffahs 100 are sold or provided to users, it is envisioned that they shall be disposed of after limited use. That is, the luffah 100 is disposed of once the substantially dry, water-soluable cleansing and/or moisturizing agent is exhausted. Such disposability prevents the spread of bacteria, germs and the like. The cost of fabricating the luffahs 100 according to the embodiments of the present invention allows them to be easily and inexpensively replaced on a small budget. The luffahs according to the embodiments of the present invention are also ideal for travel.

Although the invention has been described in detail with reference to several embodiments, additional variations and modifications exist within the scope and spirit of the invention as described and defined in the following claims.

I claim:

1. A cleansing article comprising:
a luffah formed of a series of ruffles; and
said ruffles of said luffah at least partially coated with a substantially dry, water-soluble, cleansing and/or moisturizing agent such that said luffah may be used one or more times without an application of additional cleansing and/or moisturizing agent, said substantially dry, water-soluble, cleansing and/or moisturizing agent being concentrated at a core of the luffah such that outer portions of said ruffles are not coated with said substantially dry, water-soluble, cleansing and/or moisturizing agent, said luffah non-functional for cleansing until water is applied.

2. The cleansing article of claim 1 wherein said cleansing and/or moisturizing agent is selected from the group consisting of liquid soap, gel, bath wash or body wash.

3. The cleansing article of claim 2 wherein said liquid soap, gel, bath wash or body wash are each clear.

4. The cleansing article of claim 1 further comprising packaging configured to contain a single luffah.

5. The cleansing article of claim 1 further comprising packaging configured to contain multiple luffahs.

6. The cleansing article of claim 5 wherein the container is formed of a plastic and is vacuum-sealed.

7. The cleansing article of claim 5 wherein the packaging includes multiple spacers to separate the contained luffahs.

8. The cleansing article of claim 1 wherein said substantially dry, water-soluble, cleansing and/or moisturizing agent is concentrated at a core of the luffah.

9. A cleansing article comprising:
a luffah having a plurality of ruffles and a handling string; and
said ruffles of said luffah at least partially coated with a substantially dry, water-soluble, cleansing and/or moisturizing agent such that said luffah is usable at least one time without an application of additional cleansing and/or moisturizing agent, said substantially dry, water-soluble, cleansing and/or moisturizing agent being concentrated at a core of the luffah such that outer portions of said ruffles are not coated with said substantially dry, water-soluble, cleansing and/or moisturizing agent, said luffah non-functional for cleanings until water is applied.

10. The cleansing article of claim 9 wherein said cleansing and/or moisturizing agent is selected from the group consisting of liquid soap, gel, bath wash or body wash.

11. The cleansing article of claim 9 further comprising packaging configured to contain a single luffah.

12. The cleansing article of claim 9 further comprising packaging configured to contain multiple luffahs wherein said packaging is vacuum-sealed.

13. The cleansing article of claim 12 wherein the container includes multiple spacers to separate the contained luffahs.

14. The cleansing article of claim 9 wherein said substantially dry, water-soluble, cleansing and/or moisturizing agent is concentrated at a core of the luffah.

* * * * *

UNITED STATES PATENT AND TRADEMARK OFFICE
CERTIFICATE OF CORRECTION

PATENT NO.        : 7,589,053 B2
APPLICATION NO.   : 11/836701
DATED             : September 15, 2009
INVENTOR(S)       : Bruce T. Larsen et al.

It is certified that error appears in the above-identified patent and that said Letters Patent is hereby corrected as shown below:

Column 4, line 36, please delete "cleanings" and replace with -- cleansing --.

Signed and Sealed this

First Day of December, 2009

David J. Kappos
*Director of the United States Patent and Trademark Office*